United States Patent [19]
Cilia et al.

[11] Patent Number: 5,235,401
[45] Date of Patent: Aug. 10, 1993

[54] DEVICE FOR DETERMINATION OF VERY LOW CONCENTRATIONS OF ELEMENTS BY ATOMIC EMISSION SPECTROMETRY

[75] Inventors: Marcello Cilia; Maria G. Del Monte; Giuseppe Guantera; Renzo Tomellini; Sergio Caroli; Oreste Senofonte, all of Rome, Italy

[73] Assignees: Centro Sviluppo Materiali S.p.A.; Instituto Superiore di Sanita, Milan, Italy

[21] Appl. No.: 690,508

[22] Filed: Apr. 24, 1991

[30] Foreign Application Priority Data

Apr. 24, 1990 [IT] Italy ............................... 47883 A/90

[51] Int. Cl.$^5$ .................. G01N 21/67; G01N 21/68
[52] U.S. Cl. ............................. 356/311; 356/316
[58] Field of Search ........................... 356/311, 316

[56] References Cited
PUBLICATIONS

Caroli et al, "A Novel Version of the Microwave-Coupled Hollow Cathode Lamp for Atomic Emission Spectrometry", Applied Spectroscopy, vol. 41, #4, May/-Jun. 1987, pp. 579-583.

Primary Examiner—Vincent P. McGraw
Attorney, Agent, or Firm—Allegretti & Witcoff, Ltd.

[57] ABSTRACT

The device as per the invention consists of a low pressure lamp incorporating an appropriately positioned microwave generator within the cavity. With this arrangement it is possible to obtain within the low pressure lamp microwaves of power very much greater than that which can be obtained using known systems involving the introduction of microwaves via coaxial cable, and such as to ensure greater excitation of the atoms forming the plasma produced in the lamp, consequently increasing the sensitivity of the analytical apparatus and markedly lowering the detectability limit of trace elements.

4 Claims, 1 Drawing Sheet

DEVICE FOR DETERMINATION OF VERY LOW CONCENTRATIONS OF ELEMENTS BY ATOMIC EMISSION SPECTROMETRY

BACKGROUND OF THE INVENTION

The invention concerns a device for determining very low concentrations of elements by optical emission spectrometry. More precisely, it is an improvement on devices consisting of a low-pressure lamp coupled with microwave sources. Knowledge in the materials engineering field and the ever higher performance materials are called upon to provide, necessitate control of their content of elements, even as impurities, in traces and ultratraces (namely, down to concentrations in the order of nanograms per gram).

The requests reaching analytical laboratories are ever more demanding as regards the number of elements to be determined, analytical precision and detectability limits, and the time allowed for analysis, so sample preparation should be as simple and rapid as possible.

A technique that is very used is atomic emission spectrometry with a low-pressure source because it is very versatile, can determine all elements of interest simultaneously and can analyze solid, liquid and gaseous samples, while also conducting surface analyses. However, the technique suffers from somewhat poor detectability limit. Yet this limit has to be lowered continuously both for scientific reason and because of the eminently practical need to check on the presence of traces and ultratraces of elements that could influence the behavior of the materials which contain them.

Low-pressure lamps (e.g., glow lamps and hollow-cathode lamps) employ a low-pressure ionized gas discharge to erode the sample under analysis and to excite the eroded atoms, giving rise to a plasma whose luminous intensity is measured at the desired wavelength to determine the concentration of elements concerned. At the present time the power delivered by these lamps, and hence the intensity of the radiations emitted by the elements under analysis, restricts the possibility of detecting very low concentrations.

Various methods have been proposed for increasing the level of excitation of the atoms in the low-pressure plasma of these lamps. Of particular interest is one that ensures further excitation of the plasma by microwaves. In Spectrochimica Acta, Vol. 42B, pages 1169–1176, 1987 a description is given of a glow lamp reinforced by microwaves. In the case in point a microwave generator is coupled to a resonance chamber of the lamp by means of a 2.5-m long, 50-Ohm coaxial cable. The analytical limits of the lamp are from about 1.5 to 7 times better than for the same lamp without microwaves. For instance, it can detect values of 0.05 micrograms per gram in the case of chromium (425.4 nm line), 0.5 micrograms per gram where aluminum (396.2 nm line) and nickel (232.0 nm line) are concerned, and 0.6 micrograms per gram as regards titanium (364.4 nm).

In Applied Spectroscopy, Vol. 41, pages 579–583, 1987, a description is given of a hollow-cathode lamp reinforced by microwaves. Here an external generator, via coaxial cable, transmits microwaves into a Beenakker cavity interposed between the anodic and the cathodic blocks. Such instruments permit the detectability limit of the analytical system to be lowered by a reasonable amount. However, this limit is also correlated with the power of the microwaves and this is restricted by their transmission from the generator to the lamp via coaxial cable. Although the latter may be correctly matched to the length of the microwaves it still leads to there being a marked difference between the power emitted by the generator and that actually available within the lamp.

The present invention overcomes these difficulties by providing an excitation device for emission spectroscopy analysis that can lower the detection limits significantly compared with those now prevailing.

The device as per the invention consists in a low-pressure lamp complete with a parallelepiped chamber in one of whose walls is installed a microwave generator (or "magnetron") which, via a suitable antenna, emits into the chamber a field of microwaves that resonance at the center of a low-pressure plasma, already known, generated by said lamp. In other words, the device according to the present invention couples a hollow cathode lamp and a microwave generator in one and the same chamber, so that the maximum intensity of the microwaves coincides with the center of the plasma generated by the lamp.

According to the present invention, the internal dimensions of said chamber are correlated with the wavelength of the radiations emitted by the microwave generator. More precisely, it has a maximum internal dimension equal to a wavelength of the microwaves utilized, an intermediated internal dimension equal to 0.465 times said wavelength and a minimum internal dimension equal to 0.465 times the half-wavelength. Within said chamber, one of the larger faces carries the antenna of the microwave generator at a distance from one of the smaller faces equal to a third the wavelength, as well as the cathode of the lamp at a distance of 0.930 of the wavelength from said smaller wall. The internal dimensions of said chamber, as well as the positions of the antenna and the cathode, can all be varied together by a multiplication factor of n/4 of said wavelength, where n is a whole number. With this new structure for the chamber and the original arrangement of the microwave generator, much better use can be made of the power delivered by the magnetron, the detectability limits of the analytical method being lowered in a simple, repeatable manner by at least one order of magnitude compared with that ruling hitherto.

BRIEF DESCRIPTION OF THE DRAWING

The present invention will not be described in greater detail in relation to an embodiment illustrated purely by way of example and in no way limiting in FIG. 1 hereto which represents a schematic vertical section.

DETAILED DESCRIPTION OF THE PRESENT INVENTION

Figure 1:
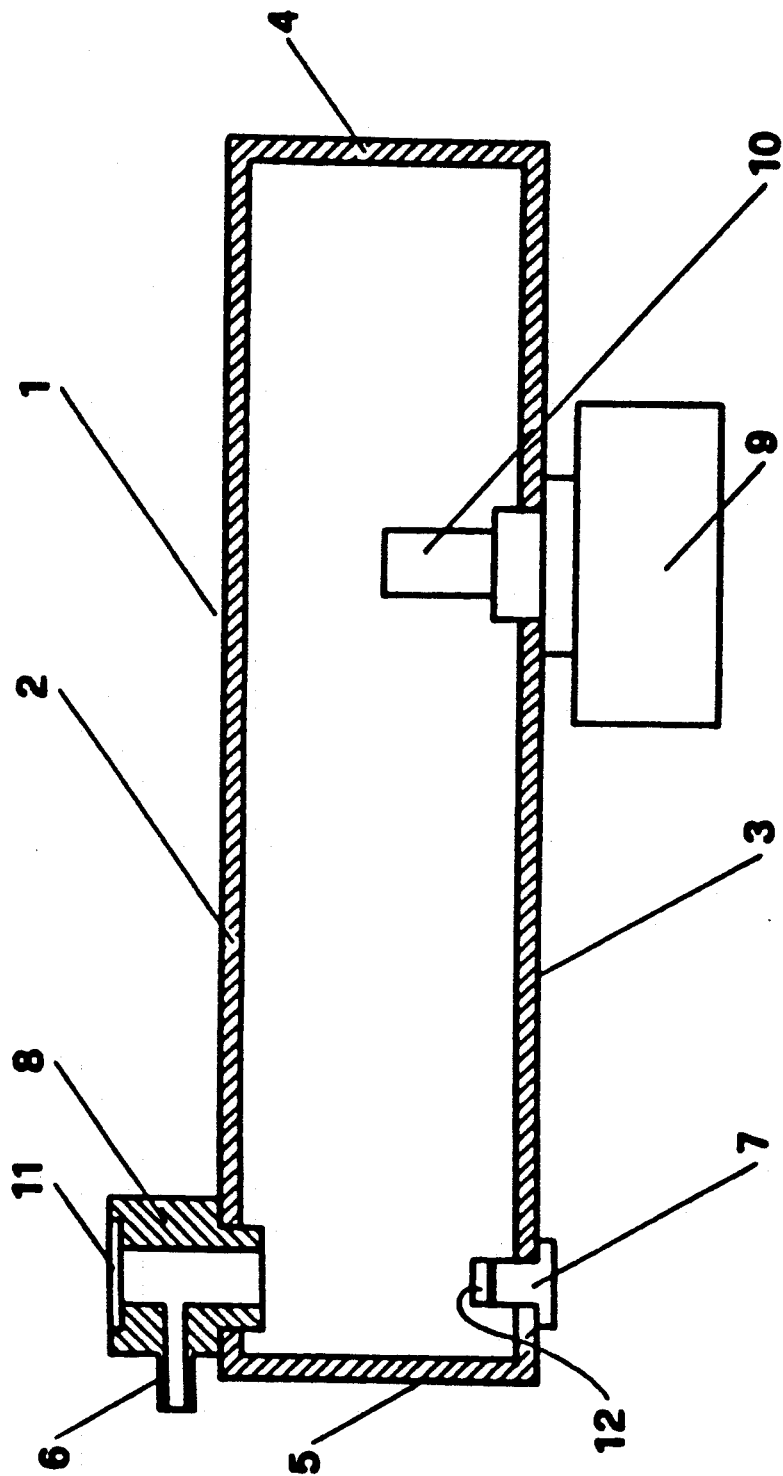

Chamber 1 is parallelepiped and has two pairs of facing walls, namely larger walls 2 and 3 and smaller walls 4 and 5, with the walls of dimension between the maximum and the minimum. On the outer part of wall 3 there is a microwave generator 9, while the relative antenna 10 protrudes into chamber 1. Wall 3 also has a cathode 7 which contains the sample 12 to be analyzed 1. Wall 2 has a hollow anode 8 with a sealed window 11 that is transparent to the lamp's emissions, on the same axis as cathode 7. Provision is made form a duct 6 for the creation of a vacuum and/or for leading gas into chamber 1.

If L is the distance between walls 4 and 5, equivalent to the wave length of the radiation emitted by the magnetron, antenna 10 is placed as a distance from wall 4 equal to a third of L, while cathode 7 is set at 0.930 L from said wall.

In operation, by means of duct 6 a given gas at low pressure is introduced and/or said gas is made to circulate at low pressure within chamber 1. Between cathode 7 (and sample 12) and anode 8 a potential difference is created so as to generate a plasma in the space between them. Said plasma erodes the surface of sample 12, liberating atoms which are drawn into the plasma where they are duly excited. At the same time the magnetron emits microwaves into the chamber. Chamber 1 is so dimensioned and the mutual positions of the antenna of the magnetron and the cathode are so fixed that the microwave beam resonates in the plasma existing between cathode 7 and anode 8. In this way the atoms removed from the sample and present in the plasma can be further excited by the microwaves, thus enabling very low concentrations of elements in the sample to be detected, because nearly all the magnetron's emission power is utilized.

The device as per the invention has been tried and the results obtained are compared below with published data (op. cit., Spectrochimica Acta, 1087) and with data obtained by the inventors using a hollow cathode connected to a separate microwave generator via a coaxial cable. These data will be published in one of the coming number of Spectorchimica Acta, Part B.

| | Detection Limits (ppm) | | |
|---------|-----------|-----------------|-----------|
| Element | Published | To be Published | Invention |
| Al | 0.1 | 0.05 | 0.005 |
| As | — | 0.024 | 0.002 |
| Cu | 0.3 | 0.05 | 0.001 |
| Si | 0.4 | 0.028 | 0.002 |
| Ti | 0.6 | 0.09 | 0.004 |

While we have shown and described a presently preferred embodiment of the present invention, it will be understood that the invention is limited only by the following claims and their equivalents.

We claim:

1. A low pressure lamp device fitted with a cathode containing a sample to be analyzed and an anode facing the cathode, coupled to a microwave source for the determination of very low concentrations of elements by optical emission spectroscopy, characterized by the fact of being formed by a parallelepiped chamber having a pair of larger walls, and a pair of smaller walls and having a maximum internal dimension equal to a wavelength of the microwaves utilized, and a minimum internal dimension equal to 0.465 times a half-wavelength, in which one of said larger faces carries a microwave generator with an antenna protruding inside said chamber at a distance from one of said smaller walls equal to one third of said wavelength, said cathode being positioned on one of said larger walls at a distance from said smaller wall equal to 0.930 time said wavelength.

2. A device as per claim 1, characterized by the fact that said internal dimensions of said parallelepiped chamber as well as the positions of said antenna and of said cathode can all be varied together by a multiplication factor of n/4 of said wavelength, where n is a whole number.

3. A low pressure lamp device fitted with a cathode containing a sample to be analyzed and an anode facing the cathode, coupled to a microwave source for the determination of very low concentrations of elements by optical emission spectroscopy, characterized by a parallelepiped chamber having a pair of larger walls, and a pair of smaller walls and having a maximum internal dimension equal to a wavelength of the microwaves utilized, and a minimum internal dimension equal to about 0.465 times a half-wavelength, in which one of said larger walls carries a microwave generator with an antenna protruding inside said chamber at a distance from one of said smaller walls equal to about one third of said wavelength, said cathode being positioned on said larger wall at a distance from said smaller wall equal to about 0.930 times said wavelength.

4. A device as per claim 3, characterized by the internal dimensions of said parallelepiped chamber, as well as the positions of said antenna and of said cathode can all be varied together by a multiplication factor of n/4 of said wavelength, where n is a whole number.

* * * * *